United States Patent
Grootjans et al.

(10) Patent No.: US 9,518,936 B2
(45) Date of Patent: Dec. 13, 2016

(54) METHOD AND APPARATUS FOR DETERMINING LITHOGRAPHIC QUALITY OF A STRUCTURE

(71) Applicant: ASML Netherlands B.V., Veldhoven (NL)

(72) Inventors: Willem Jan Grootjans, Veldhoven (NL); Henricus Johannes Lambertus Megens, Veldhoven (NL); Jouke Krist, Veldhoven (NL); Miguel Garcia Granda, Veldhoven (NL); Lu Xu, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 14/648,457

(22) PCT Filed: Oct. 30, 2013

(86) PCT No.: PCT/EP2013/072719
§ 371 (c)(1),
(2) Date: May 29, 2015

(87) PCT Pub. No.: WO2014/082813
PCT Pub. Date: Jun. 5, 2014

(65) Prior Publication Data
US 2015/0308966 A1    Oct. 29, 2015

Related U.S. Application Data

(60) Provisional application No. 61/731,939, filed on Nov. 30, 2012.

(51) Int. Cl.
*G03B 27/54* (2006.01)
*G01N 21/956* (2006.01)
(Continued)

(52) U.S. Cl.
CPC ........ *G01N 21/95607* (2013.01); *G01N 21/47* (2013.01); *G03F 7/70133* (2013.01);
(Continued)

(58) Field of Classification Search
CPC ... G03F 7/705; G03F 7/70133; G03F 7/70625
(Continued)

(56) References Cited

U.S. PATENT DOCUMENTS 5,847,394 A    12/1998  Alfano et al.
5,975,702 A    11/1999  Pugh, Jr. et al.
(Continued)

FOREIGN PATENT DOCUMENTS

CN    1238687 C    1/2006
CN    101819384 A    9/2010
(Continued)

OTHER PUBLICATIONS

International Search Report directed to related International Patent Application No. PCT/EP2013/072719, mailed Jun. 23, 2014; 7 pages.
(Continued)

*Primary Examiner* — Hung Henry Nguyen
(74) *Attorney, Agent, or Firm* — Sterne, Kessler, Goldstein & Fox P.L.L.C.

(57) ABSTRACT

Method for determining lithographic quality of a structure produced by a lithographic process using a periodic pattern, such as a grating, detects lithographic process window edges and optimum process conditions. Method steps are: 602: printing a structure using a lithographic process using a grating pattern; 604: selecting a first characteristic, such as a polarization direction, for the illumination; 606: illuminating the structure with incident radiation with first characteristic 608: detecting scattered radiation; 610: selecting a second characteristic, such as a different polarization direc-
(Continued)

tion, for the illumination; 612: illuminating the structure with incident radiation with the second characteristic; 614: detecting scattered radiation; 616: rotating one or more angularly resolved spectrum to line up the polarizations, thus correcting for different orientations of the polarizations; 618: determining a difference between the measured angularly resolved spectra; and 620: determining a value of lithographic quality of the structure using the determined difference.

6 Claims, 12 Drawing Sheets

(51) Int. Cl.
*G03F 7/20* (2006.01)
*G01N 21/47* (2006.01)

(52) U.S. Cl.
CPC ...... *G03F 7/70558* (2013.01); *G03F 7/70625* (2013.01); *G03F 7/70641* (2013.01); *G01N 2021/4792* (2013.01); *G01N 2201/06113* (2013.01); *G01N 2201/12* (2013.01)

(58) Field of Classification Search
USPC .................. 355/52, 53, 55, 67; 356/399–401
See application file for complete search history.

(56) References Cited

U.S. PATENT DOCUMENTS

| | | | |
|---|---|---|---|
| 6,122,042 A | 9/2000 | Wunderman et al. | |
| 6,949,462 B1 | 9/2005 | Yang et al. | |
| 7,352,453 B2* | 4/2008 | Mieher | G01N 21/956 356/125 |
| 8,144,337 B2* | 3/2012 | Hamamatsu | G01B 11/303 356/600 |
| 8,223,347 B2* | 7/2012 | Smilde | G03F 7/705 356/399 |
| 2001/0030296 A1* | 10/2001 | Ishimaru | G01N 21/474 250/559.4 |
| 2011/0027704 A1* | 2/2011 | Cramer | G03F 7/70641 430/30 |
| 2011/0043791 A1* | 2/2011 | Smilde | G03F 7/70633 356/128 |
| 2011/0235038 A1 | 9/2011 | Fukazawa et al. | |
| 2012/0013881 A1 | 1/2012 | Den Boef et al. | |
| 2012/0086940 A1 | 4/2012 | Shih et al. | |

FOREIGN PATENT DOCUMENTS

| | | |
|---|---|---|
| EP | 1 628 164 A2 | 2/2006 |
| EP | 2 219 078 A1 | 8/2010 |
| WO | WO 02/21075 | 3/2002 |

OTHER PUBLICATIONS

International Preliminary Report on Patentability and Written Opinion of the International Searching Authority directed to related International Patent Application No. PCT/EP2013/072719, issued Jun. 2, 2015; 10 pages.

English-language Abstract of Chinese Patent Publication No. CN 1238687C, published Jan. 25, 2006; 1 page.

English-language Abstract of Chinese Patent Publication No. CN 101819384A, published Sep. 1, 2010; 2 pages.

First Chinese Office Action (with English-language translation) Chinese Patent Publication No. 201380062245.0, published Apr. 25, 2016; 30 pages.

\* cited by examiner

METHOD AND APPARATUS FOR DETERMINING LITHOGRAPHIC QUALITY OF A STRUCTURE

CROSS-REFERENCE TO RELATED APPLICATIONS

This application claims the benefit of U.S. provisional application 61/731,939, which was filed on Nov. 30, 2012, and which is incorporated herein in its entirety by reference.

FIELD

The present invention relates to a method of determining lithographic quality of a structure produced by a lithographic process using a periodic pattern, inspection apparatus, lithographic apparatus, lithographic cells and device manufacturing methods, useable for example in qualifying the process of a lithographic or other processing apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Current methods to evaluate printability of structures processed by a lithographic process that uses formation of a periodic image on a substrate may be based on the technique known as CDSEM (Critical Dimension Scanning Electron Microscopy). This is a technique in which, for example, knowing the expected dimensions of a structure, for example a photoresist grating, a dedicated Scanning Electron Microscope (SEM) is used to capture images of the grating with nanometric resolution and an image processing algorithm detects the edges of the grating lines to evaluate their Critical Dimension (CD). The behavior of CD with respect to printing conditions (namely focus and dose) can yield the edges and centre of the process window of the lithographic process.

Alternative methods can be used based in scatterometry techniques. One example of them requires the use of an angularly resolved scatterometer to reconstruct the photoresist cross-section profile based on the light scattered by the grating (CD reconstruction). This technique can provide more information than the CDSEM, but it requires additional previous knowledge of the grating characteristics and material properties.

Such methods to evaluate printability in semiconductor lithography of structures processed by a lithographic process that uses formation of a periodic image on a substrate are time-consuming and/or require a great deal of knowledge of the printed structures and underlying material stack properties.

In the case of CDSEM, it is required to dedicate a costly tool for an extended period of time in order to take images of each required target at each required point in a Focus Energy Matrix (FEM) wafer in order to build a map of the CD as function of the focus-dose conditions. These measurements are done at independent lines in the grating, for which they are highly noise sensitive.

In the case of using scatterometry tools for CD reconstruction (such as angularly resolved scatterometers) an important knowledge of the targets to be measured is needed: CD and pitch ranges, material properties, line roughness, etc. In order to take all these parameters into consideration, a process of CD recipe creation is needed, which typically takes 8 to 40 man-hours and requires additional thin-film and CDSEM measurements.

Currently, for lithography process monitoring products, scatterometry methods are preferred providing much better throughput performance comparing to CDSEM. However, CDSEM is still used during the setup phase, especially for determination of edges and centre of the process window of the lithographic process. The mixed use of two different such metrology approaches adds extra complexity and requires longer setup lead time.

SUMMARY

It is desirable to avoid the requirement to have previous knowledge of the structure and underlying material stack properties, to have a faster way to evaluate printability in comparison with CDSEM and to have a more reliable result in evaluating marginal printability.

According to a first aspect, there is provided a method of determining lithographic quality of a first structure processed by a lithographic process that uses formation of a periodic image on a substrate, the method comprising the steps of: (a) illuminating the first structure with incident radiation with a first characteristic; (b) measuring intensity of radiation scattered by the first structure; (c) performing a comparison using the measured intensity; and (d) determining a value of lithographic quality of the first structure using results of the comparison.

According to an aspect, there is provided an inspection apparatus configured for determining lithographic quality of a first structure processed by a lithographic process that uses formation of a periodic image on a substrate, the inspection apparatus comprising: an illumination system configured to illuminate the first structure with incident radiation with a first characteristic; a detection system configured to measure intensity of radiation scattered by the first structure; and a processor configured to: perform a comparison using the measured intensity; and determine a value of lithographic quality of the first structure using results of the comparison.

According to an aspect, there is provided a lithography apparatus comprising an exposure system and an inspection apparatus, the inspection apparatus configured for determining lithographic quality of a first structure processed by a lithographic process that uses formation of a periodic image on a substrate, the inspection apparatus comprising: an illumination system configured to illuminate the first structure with incident radiation with a first characteristic; a detection system configured to measure intensity of radiation scattered by the first structure; and a processor configured to: perform a comparison using the measured intensity; and determine a value of lithographic quality of the first structure using results of the comparison.

According to an aspect, there is provided a lithographic cell comprising: a lithographic apparatus comprising an exposure system; and an inspection apparatus, the inspection apparatus configured for determining lithographic quality of a first structure processed by a lithographic process that uses formation of a periodic image on a substrate, the inspection apparatus comprising: an illumination system configured to illuminate the first structure with incident radiation with a first characteristic; a detection system configured to measure intensity of radiation scattered by the first structure; and a processor configured to: perform a comparison using the measured intensity; and determine a value of lithographic quality of the first structure using results of the comparison.

According to an aspect, there is provided a computer program product containing one or more sequences of machine-readable instructions for determining lithographic quality of a first structure processed by a lithographic process that uses formation of a periodic image on a substrate, the instructions being adapted to cause one or more processors to perform a method according to the first aspect.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention FIG. 1 depicts a lithographic apparatus.

Figure 1:
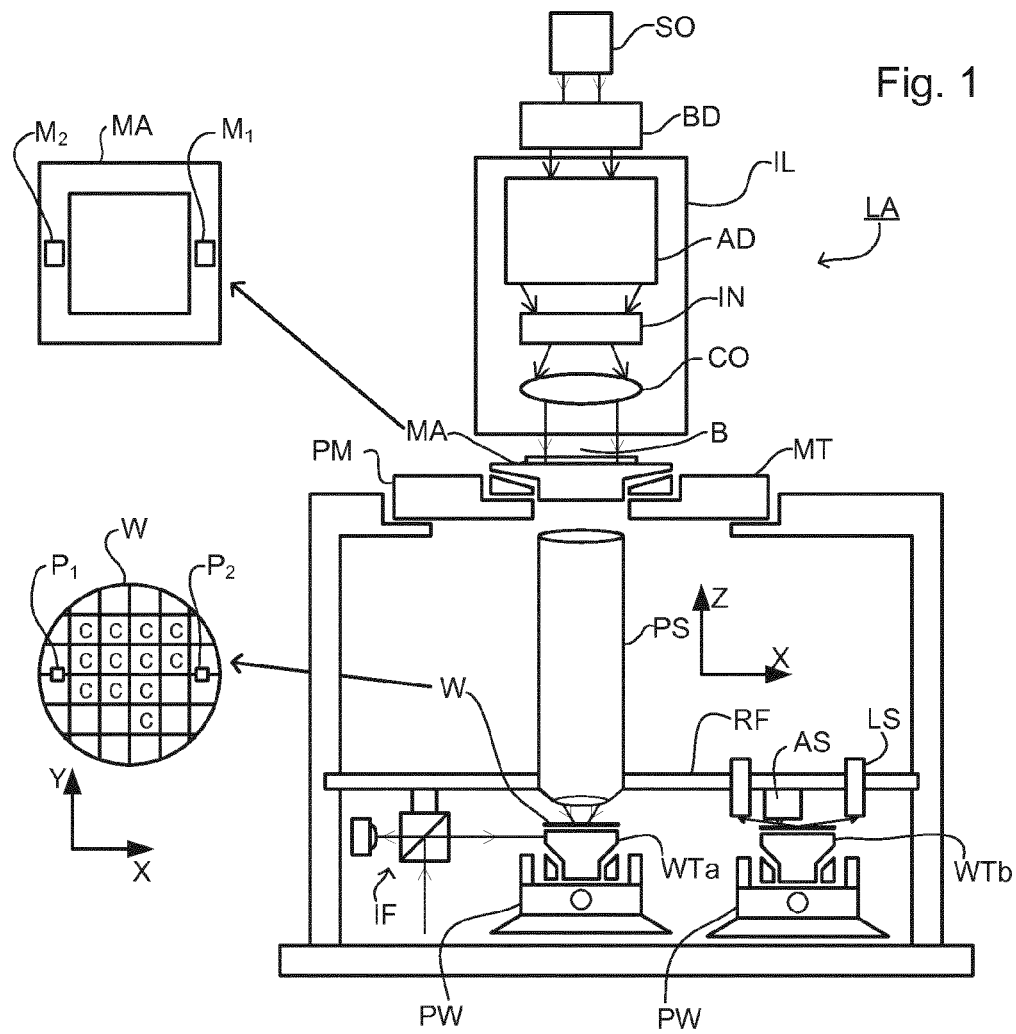

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the clauses appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically shows a lithographic apparatus LAP including a source collector module SO according to an embodiment of the invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:
1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above. Combinations and/or variations on the above described modes of use or entirely different modes of use may also be employed.

Figure 2:
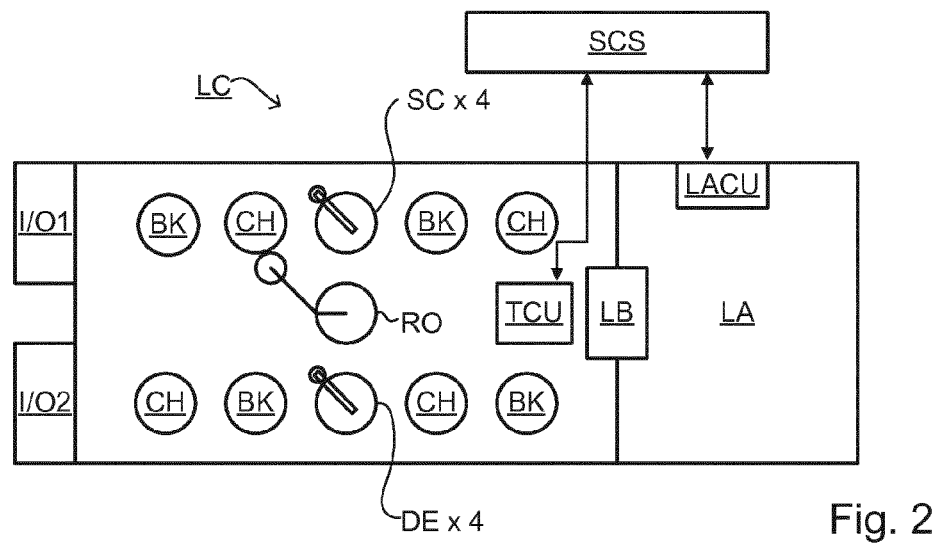
FIG. 2 depicts a lithographic cell or cluster including the apparatus of FIG. 1.

FIG. 2 depicts a lithographic cell or cluster including the apparatus of FIG. 1. As shown in FIG. 2, the lithographic apparatus LA forms part of a lithographic cell LC, also sometimes referred to a 'lithocell' or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus or metrology tool is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
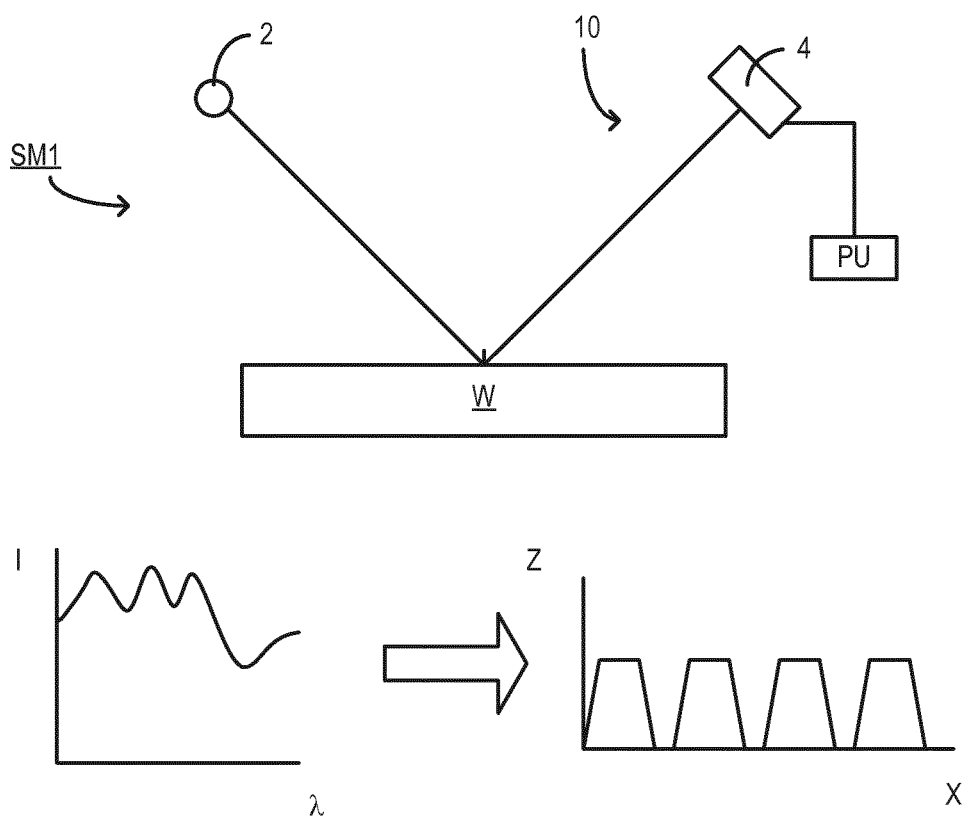
FIG. 3 depicts a first scatterometer.

FIG. 3 depicts a scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
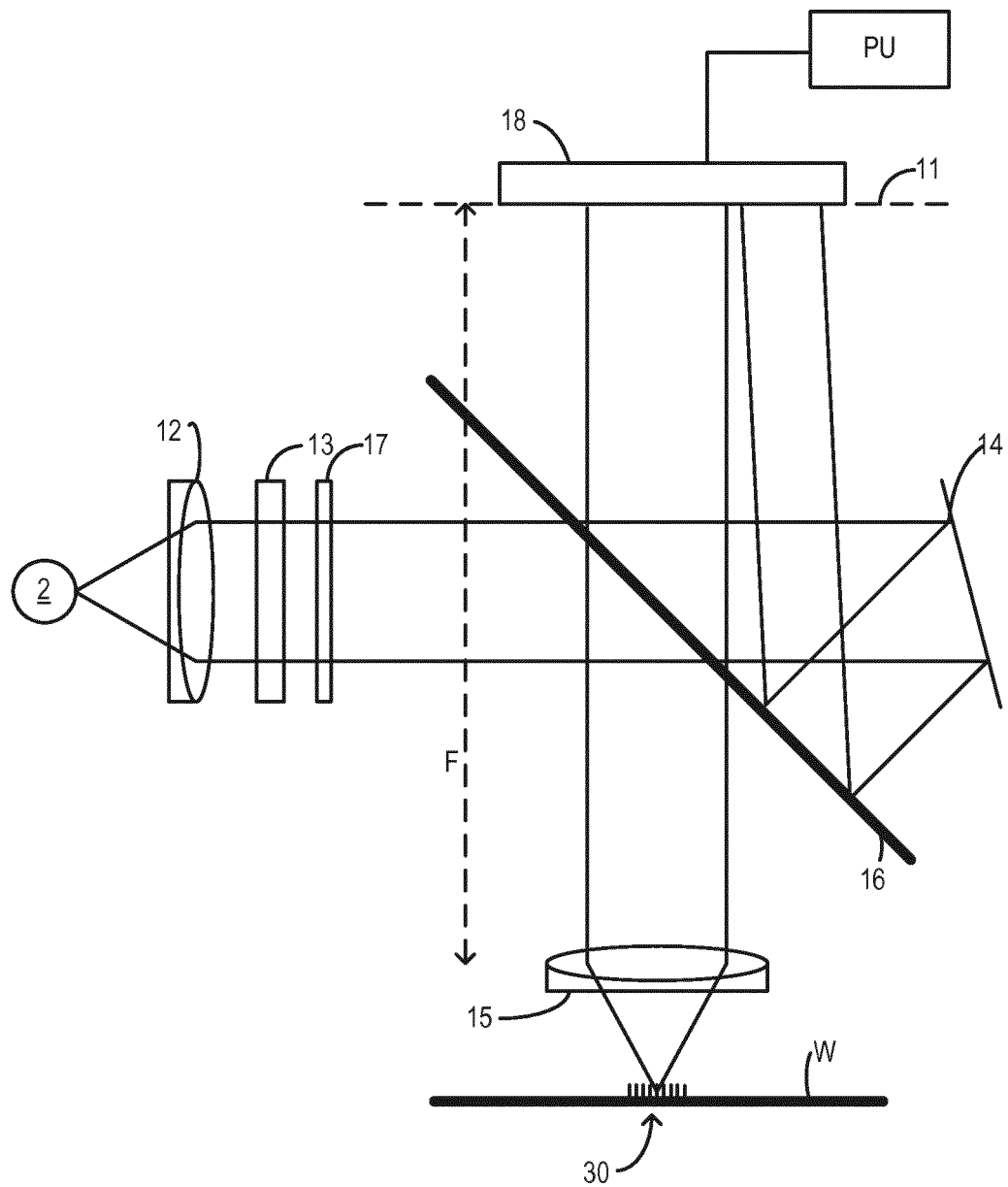
FIG. 4 depicts a second scatterometer.

Another scatterometer is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. In this example the polarizer 17 is controlled by the processing unit PU to select different orientations of polarization, for example either TM (transverse magnetic) or TE (transverse electric) polarized radiation, for illumination of the substrate W. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

A key component of accurate lithography is an ability to calibrate individual lithographic apparatus. In addition to general parameters affecting the whole substrate area, it is known to map and model the error 'fingerprint' of an individual apparatus across the substrate area. This fingerprint, which can be established in terms of focus, dose and/or alignment, can be used during exposure to correct the idiosyncrasies of that apparatus, and thereby achieve a more accurate patterning.

Improvements to the apparatus's focus and overlay (layer-to-layer alignment) uniformity have recently been achieved by the applicant's Baseliner™ scanner stability module, leading to an optimized process window for a given feature size and chip application, enabling the continuation the creation of smaller, more advanced chips. The scanner stability module may automatically reset the system to a pre-defined baseline each day. To do this it retrieves standard measurements taken from a monitor wafer using a metrology tool. The monitor wafer is exposed using a special reticle containing special scatterometry marks. From that day's measurements, the scanner stability module determines how far the system has drifted from its baseline. It then calculates wafer-level overlay and focus correction sets. The lithography system then converts these correction sets into specific corrections for each exposure on subsequent production wafers.

Lithographic quality is a measure of the printability of structures using a lithographic process, as described in further detail below with reference to FIG. 12. An example technique uses images captured by an angularly resolved scatterometry tool to perform a fast measurement of the quality of a grating.

Figure 5:
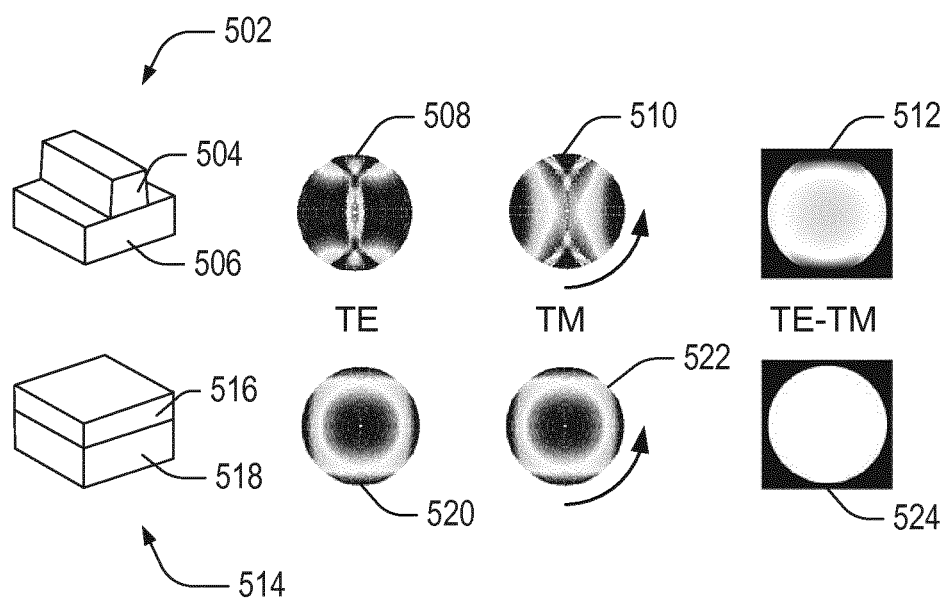
FIG. 5 illustrates operation of the method of determining lithographic quality using the subtraction of different polarization images as metric.

FIG. 5 illustrates operation of an example method of determining lithographic quality, in this example grating quality, using the results of subtraction of different polarization images as metric. With reference to FIG. 5, when the radiation is diffracted by a line/space grating, a portion of which is shown 502 with a line 504 on a substrate 506, the diffraction pattern that the scatterometry tool captures is polarization sensitive. Therefore, if two angularly resolved scatterometer pupil spectra are measured using two polarizations (for example the perpendicular polarizations, Transverse Electric, TE, and Transverse Magnetic, TM) the resulting spectrum image 508 for TE and 90° rotated spectrum image 510 for TM can be subtracted one from another and a root mean square (RMS) average of the resulting difference image 512 can be evaluated yielding an intrinsically non-zero lithographic quality value, referred to herein for this example as grating quality, GQ.

If the images have been taken on a thin film stack, a portion of which is shown 514 with a continuous film 516 on a substrate 518 (thus no grating is present, but just the continuous film instead), there is no polarization sensitivity of the diffracted light. So, after measuring two angularly resolved scatterometer pupil spectra using two polarizations (for example TE and TM), the resulting spectra images 520 and 522 can again be subtracted one from another other and a root mean square (RMS) average of the resulting difference image 524 will result in a value close to zero. Only image noise will make it different from zero.

If the images have been taken on a grating with a certain degree of defects (very low lines, extremely low side wall angle (SWA), notable bridging between the lines, broken or fallen lines, etc.) the contrast between the two polarization images will be affected, yielding an RMS result between those of the thin film and the perfect grating.

Thus, the magnitude of the resulting RMS, GQ, provides information of the grating quality that can be obtained with a scatterometry tool without using any model or previous knowledge of the measured structures.

The RMS average is used as a particular example, but the same principle can be applied to any printing quality metric that can be generated from the measurements performed with a scatterometry tool resulting in a discrepancy between the measured signal and the predicted signal in the absence of grating.

The "difference" between the measured intensities may be understood in the sense of "dissimilarity" or "distinction" and is not limited to the sense of mathematical subtraction. A metric in which not the mathematical difference but the mathematical division is performed would also give a valid result. In other words, the difference may be thus calculated by subtraction as described above, or by any other method for determining the dissimilarity between two signals, such as division.

The measured "difference" between spectra may be converted in order to qualify the lithographic quality. A way to obtain that conversion is to use a "threshold" of, for example, 0.02 in the RMS, although this value is stack dependent. Other procedures for calculation of the quality may be used when the method is applied to different lithographic stacks.

Moreover, if this metric is evaluated as function of the focus-dose conditions on a FEM (Focus-Exposure Matrix) wafer, the printability limits can be obtained, as discussed further below, with reference to FIGS. 8 and 9.

Figure 6:
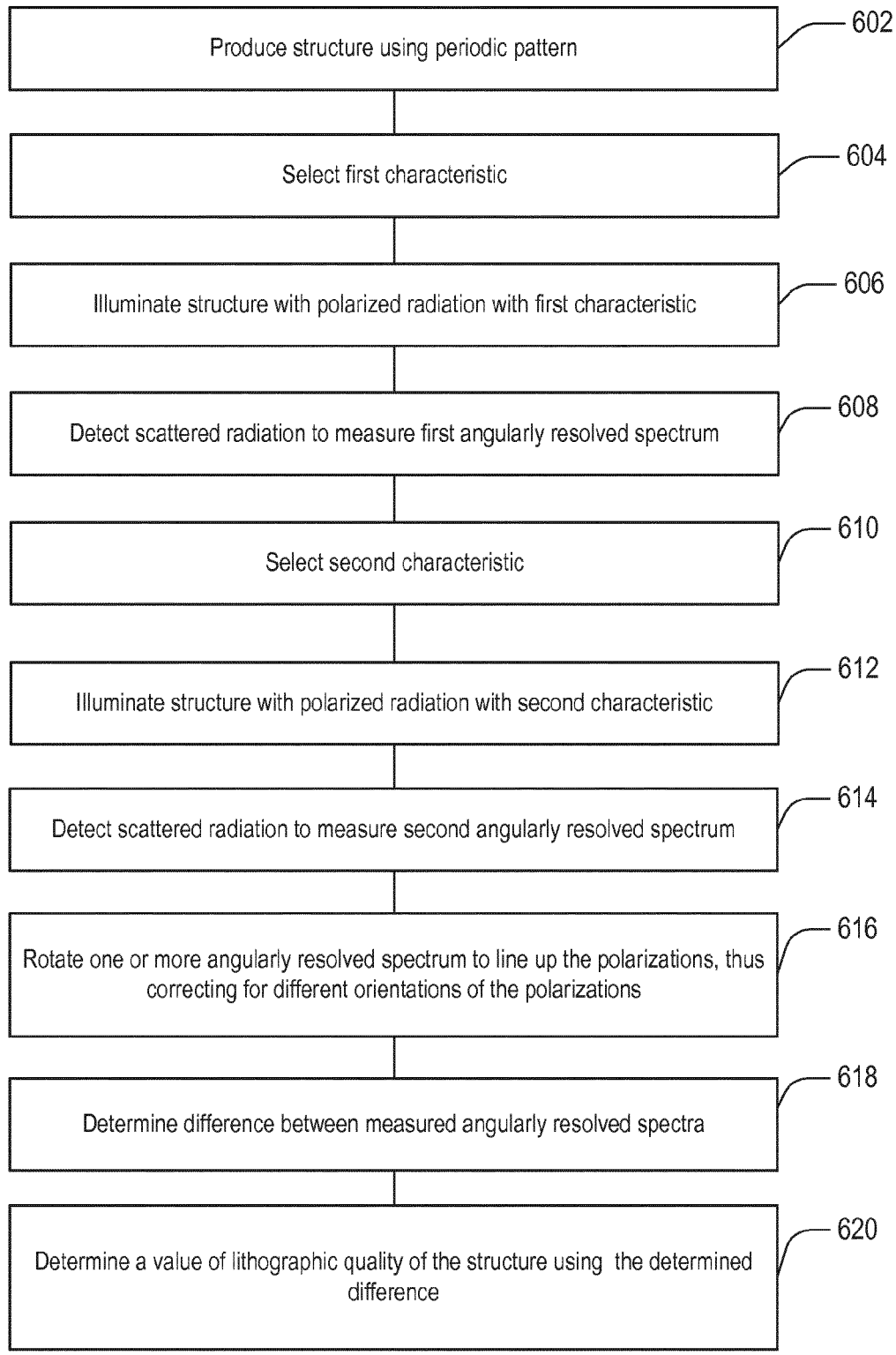
FIG. 6 is a flowchart of a method according to an example for determining lithographic quality of a structure using illumination radiation with first and second characteristics.

FIG. 6 is a flowchart of an example method for determining lithographic quality of a structure produced by a lithographic process using a periodic pattern and illumination radiation with first and second characteristics. It is to be appreciated the method may not occur in the order shown, or require all steps that are discussed.

In step 602: producing a structure using a lithographic process and using a periodic pattern, such as a grating, on a substrate.

In step 604: selecting a first characteristic, such as a polarization direction, for the illumination.

In step 606: illuminating the structure with polarized radiation with the first characteristic.

In step 608: detecting intensity of radiation scattered from the structure, arising from illumination with the first characteristic, for example to measure a first angularly resolved spectrum.

In step 610: selecting a second characteristic, such as a polarization direction, for the illumination.

In step 612: illuminating the structure with polarized radiation with the second characteristic.

In step 614: detecting intensity of radiation scattered from the structure, arising from illumination with the second characteristic, for example to measure a second angularly resolved spectrum.

In step 616: rotating one or more angularly resolved spectrum to line up the polarizations, thus correcting for the different orientations of the polarizations.

In step 618: performing a comparison using the measured intensity to determine a difference between at least two of the measured angularly resolved spectra.

In step 620: determining a value of lithographic quality of the structure using the determined difference. The value of lithographic quality may be represented as a score, for example a grating quality score.

In the examples described with reference to FIGS. 5 and 6, polarized radiation was used for illuminating the structure. However, non-polarized light may be used as it may result in some contrast between structures having different lithographic quality, for example grating and non-grating structures. For example, for a grating with pitch larger than half of the wavelength, and using an angularly resolved approach, high order diffraction may be present in the angularly resolved spectrum pupil also with unpolarized radiation illumination. This allows differentiation of a printed grating from a not-printed grating situation, by determining a value of lithographic quality of the structure using the determined difference between at least two of the measured angularly resolved spectra. When a grating does not produce high diffraction orders (with a grating pitch smaller than half the wavelength) unpolarized light can be less efficient in picking up the differences in reflection coefficients arising from the different combinations of angle of incidence and orientation of grating along the angularly resolved spectrum pupil. When using unpolarized illumination radiation, different rotations of a direction of periodicity of the periodic image in a plane of the substrate relative to the incident radiation may be used, the rotation being around an axis perpendicular to the plane of the substrate.

Figure 7A:
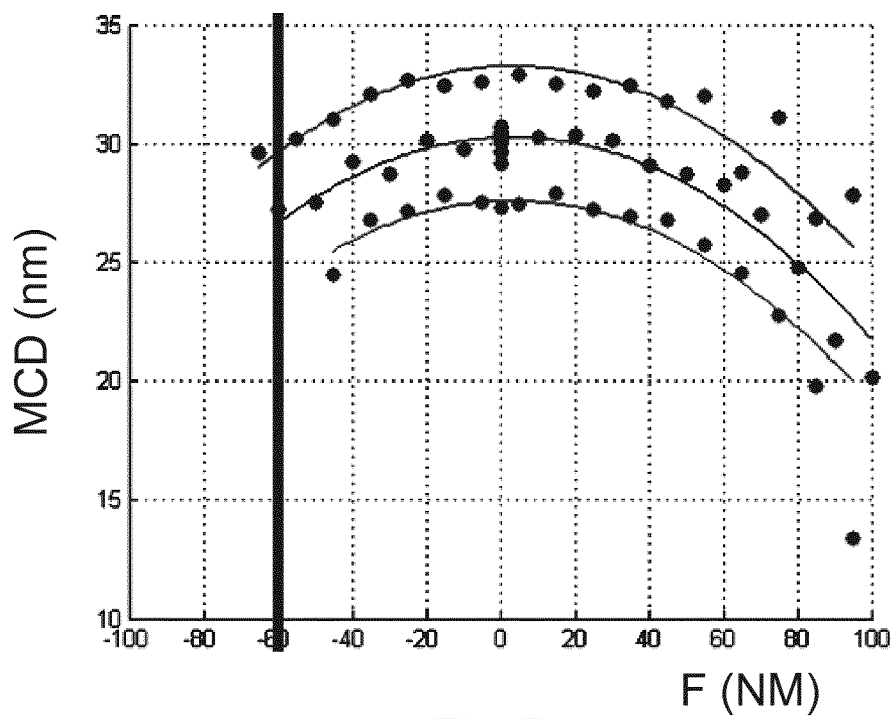
FIGS. 7a and 7b are graphs demonstrating the application of an example with actual measured data for a range of focus settings.
Figure 7B:
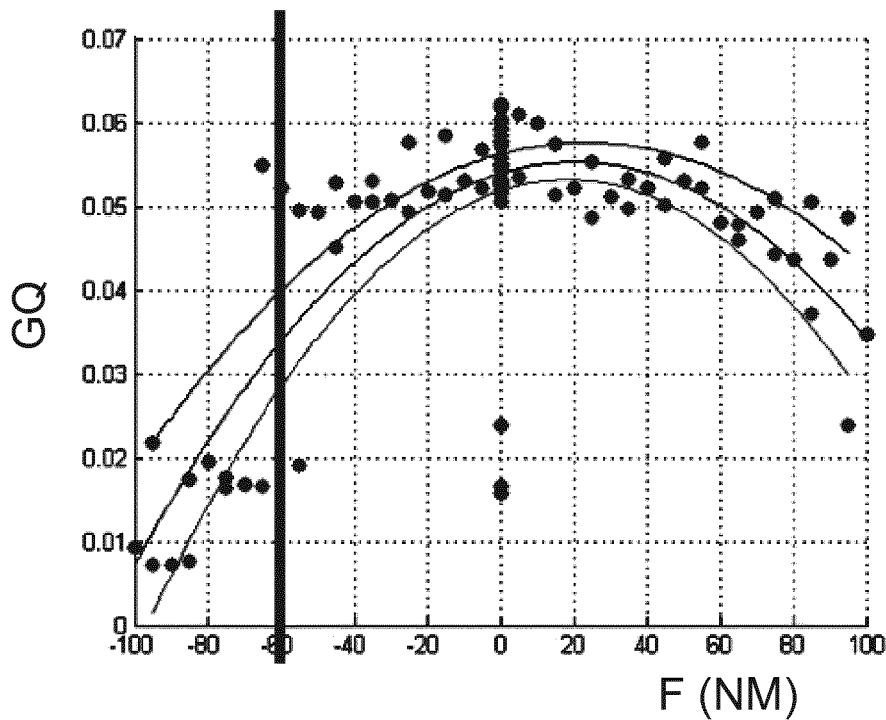

FIGS. 7a and 7b are graphs demonstrating the application of an example with actual measured data for a range of focus settings and three different exposure doses. FIG. 7a plots the results of conventional angularly resolved scatterometry median critical dimension, MCD, obtained by reconstruction, verses focus, F, showing an abrupt edge of the process window at a focus setting of −60 nm FIG. 7b plots the lithographic quality, in this example the grating quality RMS metric, GQ, of structures measured according to an example. FIG. 7b shows a steep change in grating quality at the edge of the process window at −60 nm focus setting.

Figure 8:
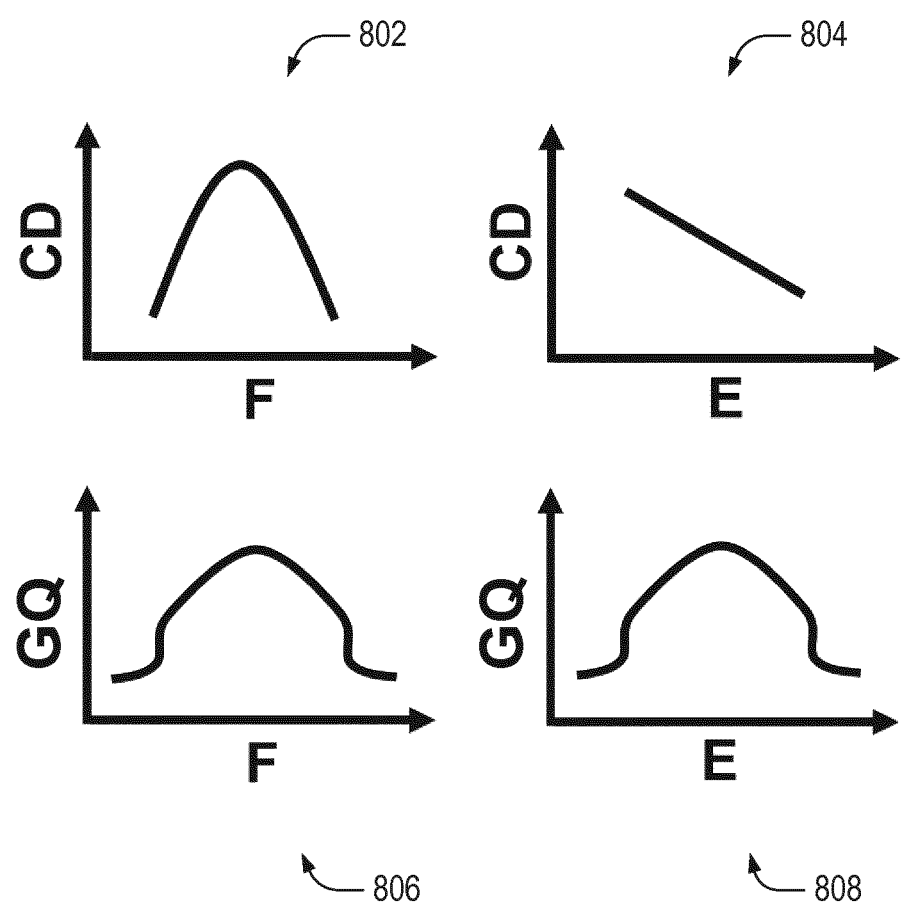
FIG. 8 illustrates an application of an example in determining the process window and optimum process conditions of a lithographic process.

FIG. 8 illustrates an application of an example in determining the edges and center of a process window of a lithographic process. Examples allow detecting not only the process window edges, as illustrated in FIG. 7b, but also the grating behavior within the process window. FIG. 8 shows the scheme of the measurements performed to find the BEBF conditions in a lithographic process being introduced into production. Graph 802 schematically illustrates conventional CDSEM measurements of critical dimension, CD, for different focus settings, F, that are used to find the Bossung Top Focus (BTF) at the peak of the curve. Graph 804 schematically illustrates CDSEM measurements of critical dimension, CD, for different energy (dose) settings, E, used to find the energy at which an anchor target prints with the desired CD. The straight line in graph 802 that describes CD as function of E for the CDSEM case spans only between the energy values in which the grating quality shows the threshold step. Outside of those points, the printability of the lines is too bad to be fitted by the model used in the CDSEM measurement.

Graph 806 schematically illustrates how the grating quality metric, GQ, for different focus settings, F, is used to find the best printing conditions. Graph 808 schematically illustrates how the grating quality metric, GQ, is used to find the printability window as a function of different energy settings, E. In certain cases, these measurements can lead to the estimation of best energy/best focus (BE/BF) conditions.

As shown in graph 806 the grating quality metric, GQ, of a particular target changes through focus denoting the edges of the process window (where the metric falls below a certain threshold value) as well as the quality of the grating. This effect yields a maximum value where the grating is better defined and, therefore, points to the best focus.

In a similar way, as shown in graph 808, for a constant pitch, changing CD/pitch ratio from 0 to 1 by changing dose generates a characteristic curve of the grating quality metric which can be used to evaluate the best dose of a particular target. These results for focus and dose have been confirmed by experimental evaluation.

The determination of grating quality in accordance with examples described herein may be performed as first quick step before conventional scatterometer measurements, for example for CD reconstruction. Then, if no grating is found, the further conventional measurements can be skipped, so saving measurement and analysis time.

Examples are not limited to the case of two polarization states as first and second illumination characteristics. Variables that can be modified to produce first and second characteristics of illumination are: (a) polarization of incident radiation; (b) angle of incidence of the radiation with respect to the substrate; and (c) rotation of a direction of periodicity of the periodic image in a plane of the substrate relative to the incident radiation, the rotation being around an axis perpendicular to the plane of the substrate, such as by rotation of the wafer.

Other suitable variables are scatterometer illumination dose, wavelength of the scatterometer illumination radiation and the illumination profile of the scatterometer.

The analyzed magnitude is the intensity of light scattered from the target structure. For that intensity, a metric may be selected for which a grating will create a signal when some of the above variables change whereas a thin film will not.

Some examples may not use an angularly resolved spectrum. It is also possible to have a signal from a grating using only one angle of incidence and comparing the intensity diffracted with different polarizations and different wafer orientations.

For non-angularly resolved images, (at least) two images may be used. These two images can be collected with different polarizations and with different wafer orientations (this makes up for the lack of angular resolution). In the example discussed with reference to FIG. 11, one can select a pixel of the pupil (i.e., one angle of incidence) that produces different intensity for each polarization. However, the same would hold for the case of a thin film. In order to have a zero signal from a thin film in in such a non-angularly resolved measurement, the wafer may be rotated by 90 degrees between the measurement of the images.

Although examples are described with respect to a printing of gratings, examples can be applied to any periodic structure that shows asymmetry in one direction. This includes typical test targets used in wafer metrology such as "brick walls" or an asymmetric network of contact holes.

Figure 9:
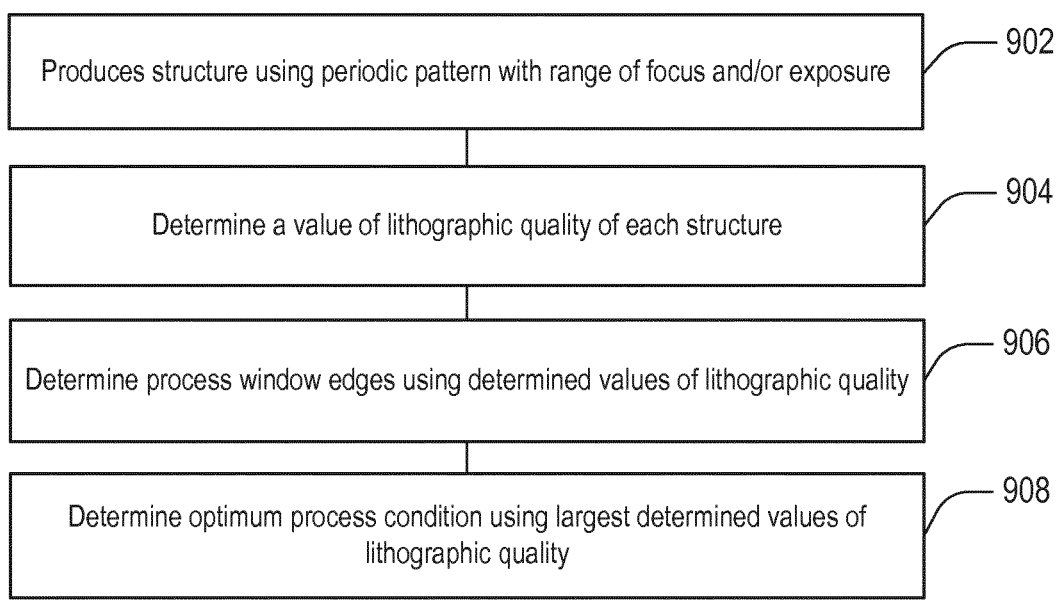
FIG. 9 is a flowchart of a method according to an example for determining the process window and optimum process conditions of a lithographic process.

FIG. 9 is a flowchart of a method according to an example for determining the process window and Best Exposure/Best Focus of a lithographic process. It is to be appreciated the method may not occur in the order shown, or require all steps that are discussed.

In step 902: print structure using periodic pattern with range of focus and/or exposure.

In step 904: determine a value of lithographic quality of each structure, using a process as described with reference to FIG. 6.

In step 906: determine the process window edges using determined values of lithographic quality (for example grating quality as described with reference to FIG. 8).

In step 908: determine the Best Energy/Best Focus using largest determined values of lithographic quality (again as described with reference to FIG. 8).

Figure 10:
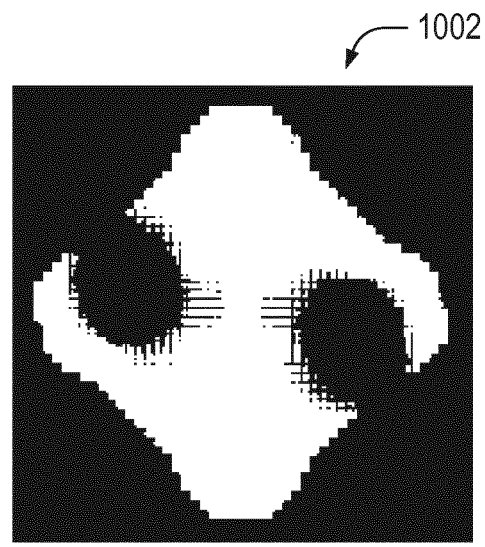
FIG. 10 is an angularly resolved spectrum of a grating placed under an angle of 45 degrees with respect to linearly polarized light.

With reference to FIG. 10, an example suitable for determining the presence of a grating includes illuminating the structure twice with the same polarization but changing the rotation of the substrate under the lens. This works because the direction of polarization with respect to the grating is significant. The simulated angular resolved spectrum in the image 1002 of FIG. 10 is of a grating placed under an angle of 45 degrees with respect to the linearly polarized light. There is a clear up/down or left/right asymmetry in the pupil which would not be there if there was only a thin film stack. In this example, the angle of incidence also plays a role. If the polarization is aligned with the grating then rotating the angle of incidence around the optical axis one direction or the other will have the same effect because the change in obliqueness of the incoming beam will be the same. This is not the case when the angle of incidence is not aligned with the grating. Thus, it is not only the direction of polarization with respect to the grating that is significant, but also the angle of incidence of the incoming polarized radiation.

For examples using angularly resolved scatterometry, such as discussed with reference to FIG. 10, the intensity measurement can be performed with only one image. If linearly polarized light impinges on the grating with 45 degree orientation with respect to the grating direction, the recorded pupil will be intrinsically asymmetric. This means that applying a mirror transformation to the image and comparing it with itself will be enough to distinguish the fingerprint of a grating.

Figure 11:
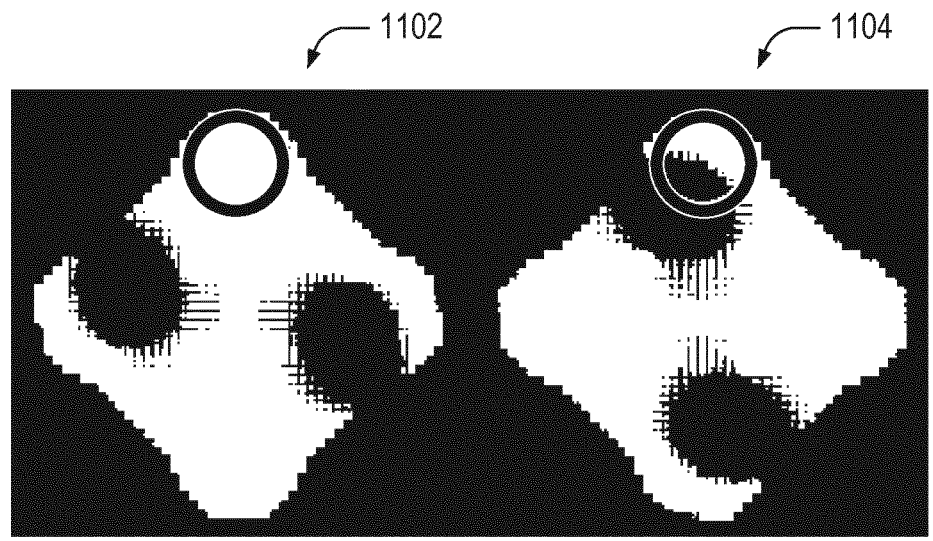
FIG. 11 illustrates angularly resolved spectra of a grating placed under an angle of 45 degrees with respect to linearly polarized light for two different polarizations.

With reference to FIG. 11, the spectra 1102 and 1004 for a grating under angle of 45 degrees for two different polarizations. The parts highlighted by the black circle represent some angle of incidence which has a different intensity. This would still hold for a non angle resolved spectrum which is illuminated under that particular angle of incidence. This means that in this example the spectrum being angle resolved is not used for the grating qualification Thus, in examples, different combinations of polarization, angle of incidence and rotation of substrate are used for which gratings give a difference in measured intensity and a thin film stack does not give such a difference in measured intensity. The different combinations may be actualized sequentially (for example using the polarizations) or simultaneously (for instance for the angles of incidence as discussed with reference to FIG. 10. A further example includes measuring the polarization state of the reflected light instead of the intensity. If we look at an oblique grating and an oblique angle of incidence then linearly polarized light will not be reflected as linearly polarized light if there is a grating and it will be reflected as linearly polarized light if there is no grating.

Figure 12:
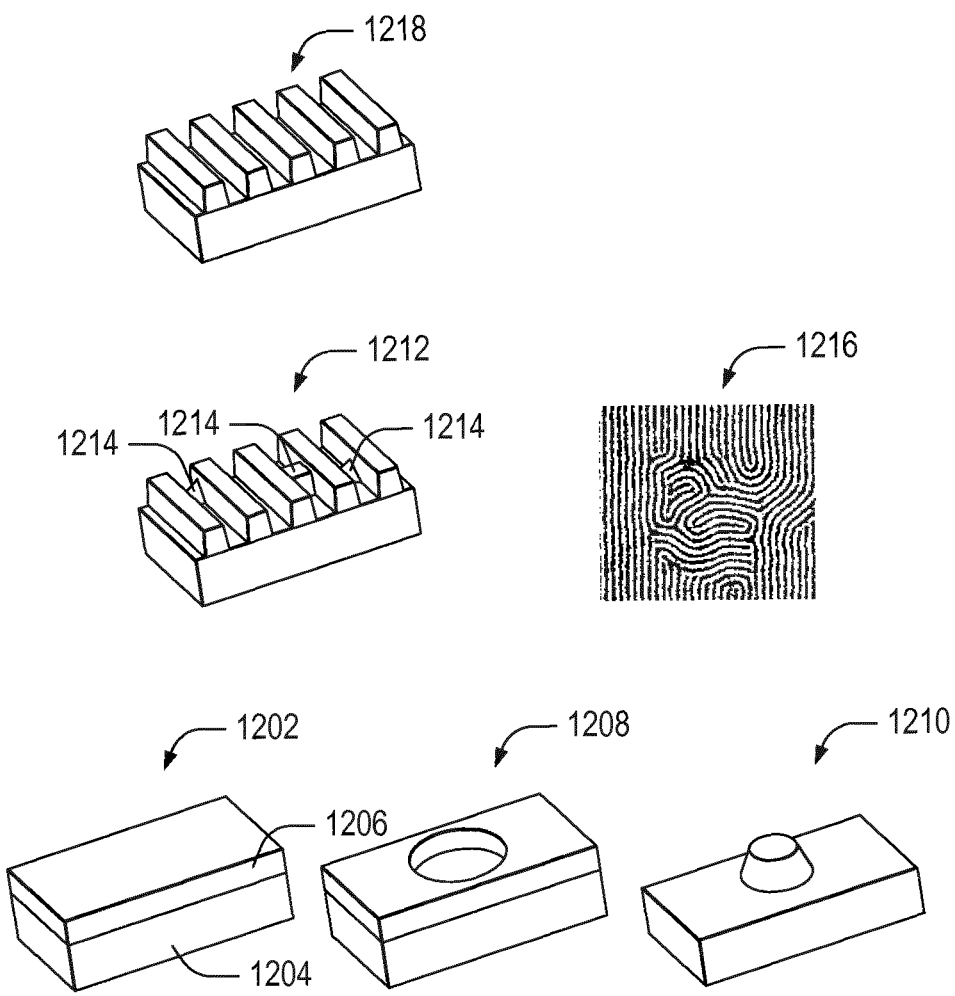
FIG. 12 illustrates structures with a range of lithographic quality scores.

FIG. 12 illustrates structures with a range of lithographic qualities, each giving rise to a corresponding grating quality score. In FIG. 12, the grating quality score, or grating quality, obtainable for the illustrated structures increases for structures going from the bottom to the top of the drawing. Sample 1202 is a schematic section of a substrate 1204 with a thin film structure 1206 on its upper surface. Sample 1208 is a rectangular section of a substrate with a square grid of symmetric contact holes in the upper thin film. Sample 1210 is a rectangular section of a substrate with a square grid of symmetric round features. Samples 1202, 1208 and 1210 all yield a low grating quality, because in each case there is no surface structure asymmetry in the plane of the substrate. Sample 1202 could be, for example, a substrate with a resist layer where the focus setting of a grating pattern exposure has been very poor. Therefore after the develop step the upper resist layer 1206 has no pattern in it. Sample 1212 is a partially printed grating with defects 1214, resulting in imperfect surface structure asymmetry in the plane of the substrate. The grating quality of sample 1212 is higher than for sample 1202, and may be above a certain threshold, but could be higher without the defects 1214.

Sample 1216 is a plan view of a cluster defect arising in a Directed Self-Assembly lithographic process. The grating quality of sample 1216 is less than for a uniform grating, with no defects, produced using a DSA lithographic process. Particle and bridging defects can also arise in a Directed Self-Assembly lithographic process, resulting in a lowering of the grating quality, compared to the case in an absence of such defects.

Sample 1218 has a properly printed grating structure in its upper surface with perfect surface structure asymmetry in the plane of the substrate. Sample 1218 therefore yields a maximum grating quality.

More detailed examples of structures yielding different grating qualities will now be described.

A non-printed grating (such as 1202) has a structure in which the grating periodicity is completely absent. This kind of structure scores below a defined "well-printed" threshold in a defined grating quality scale (corresponding to detector photon noise). Typical examples that would score below the threshold are: extremely collapsed lines without periodicity; no grating, only some remaining resist; and grating completely gone, only thin film present.

A poor quality grating (with bad printability) has a structure in which the line/space pattern is recognizable but several issues are present. The more severe these issues, the lower the grating quality resulting from the structures. Typical examples that would score below a well-printed grating quality threshold are: lines with severe line edge roughness (LER) that can create bridges between adjacent lines; not-completely-open trenches that show remaining resist on the trench bottom; very thin and collapsed lines that distort the periodicity of the grating; lines with severe bridging and not completely open spaces; overexposed lines with very high resist loss and a very rough top, not resembling a trapezoid; and trenches printed out of focus showing strong bridging on the top. As mentioned above, in a Directed Self-Assembly lithographic process, the grating quality becomes less in case clusters of lines are not well aligned, such as 1216 in FIG. 12, or when particle defects occur.

A well printed grating (such as 1218) has a line/space pattern in which the lines are well defined and with perfect periodicity, without roughness, with a cross section that resembles a trapezoid (two side walls and a differentiated top face) and in which the spaces between the lines are clean from photoresist. A grating with almost no line edge roughness (LER) yields a high grating quality.

Figure 13:
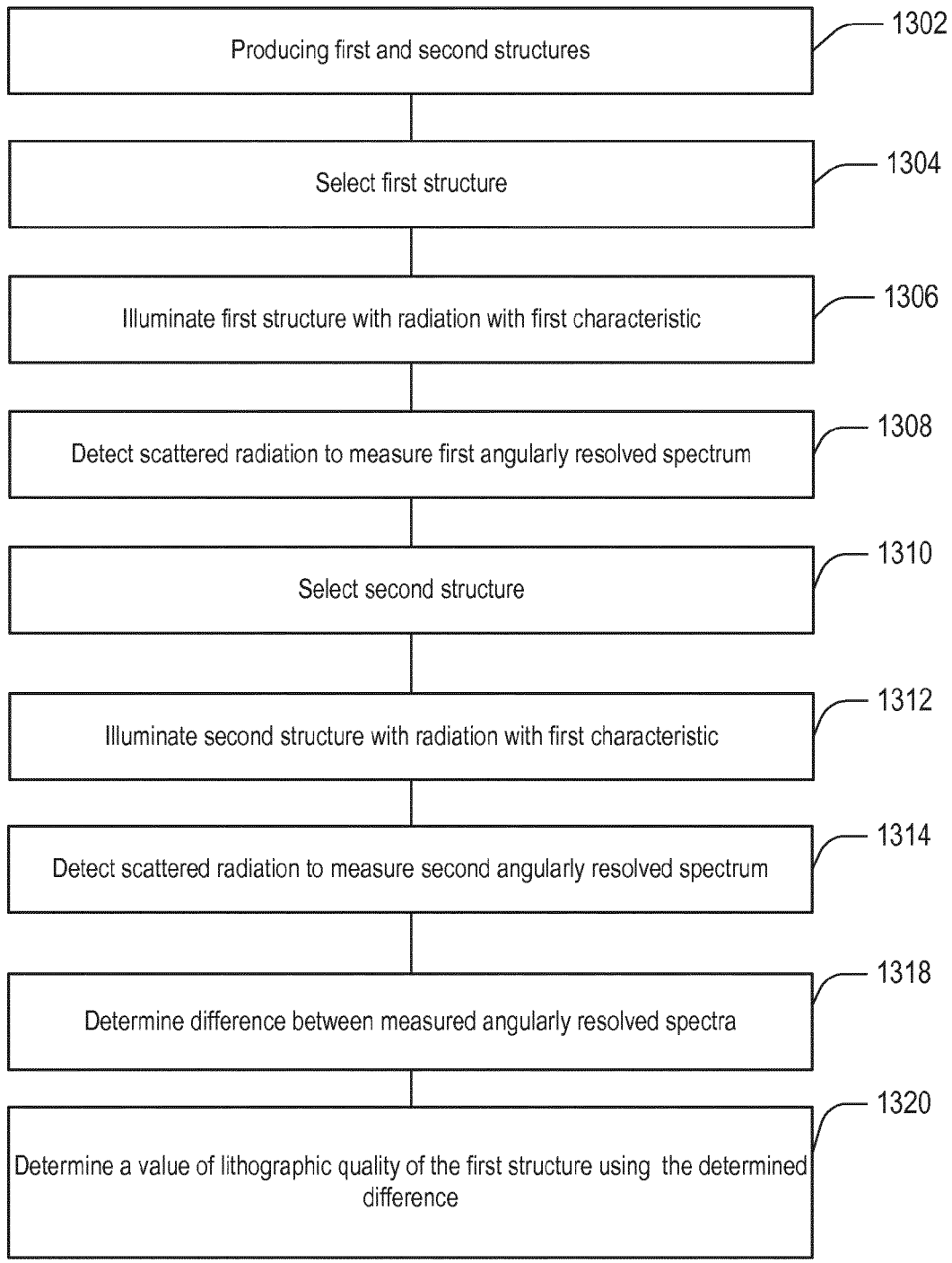
FIG. 13 is a flowchart of a method according to an example for determining lithographic quality of a structure using illumination of first and second structures.

FIG. 13 is a flowchart of a method according to an example for determining lithographic quality of a structure using a periodic pattern using illumination of first and second structures. It is to be appreciated the method may not occur in the order shown, or require all steps that are discussed.

FIG. 13 illustrates an example of another way to evaluate the lithographic quality of a structure. This involves capturing a scatterometer image by illumination of structure with radiation with a certain characteristic (for example, an angularly resolved pupil with TE polarization) and comparing the captured image with another scatterometer image. The other scatterometer image is obtained from illuminating with radiation with exactly the same characteristic a different structure used as reference (for example, a thin film area nearby the first structure on the substrate). This allows detection of the printing of structures, such a square grid of round contact holes 1208 as discussed with reference to FIG. 12, that do not present a contrast when measured using the method as described with reference to FIG. 16.

In step 1302: producing first and second structures using a lithographic process on a substrate and using a periodic pattern, such as a grating, for producing the first structure.

In step 304: selecting the first structure for illumination, such as by moving a stage supporting the substrate.

In step 1306: illuminating the first structure with radiation with a first characteristic, such as TE polarization.

In step 1308: detecting intensity of radiation scattered from the structure, arising from illumination with the first characteristic, for example to measure a first angularly resolved spectrum.

In step 1310: selecting the second (reference) structure for illumination, such as by moving the stage supporting the substrate.

In step 1312: illuminating the second structure with radiation with the first characteristic, such as TE polarization.

In step 1314: detecting intensity of radiation scattered from the second structure, arising from illumination with the second characteristic, for example to measure a second angularly resolved spectrum.

In step 1318: performing a comparison to determine a difference between the measured angularly resolved spectra, by performing a comparison to determine a difference between the measured intensity corresponding to the first structure and the measured intensity corresponding to the second structure.

In step 1320: determining a value of lithographic quality of the structure using the determined difference. The value of lithographic quality may be represented as a score, for example a grating quality score.

Figure 14:
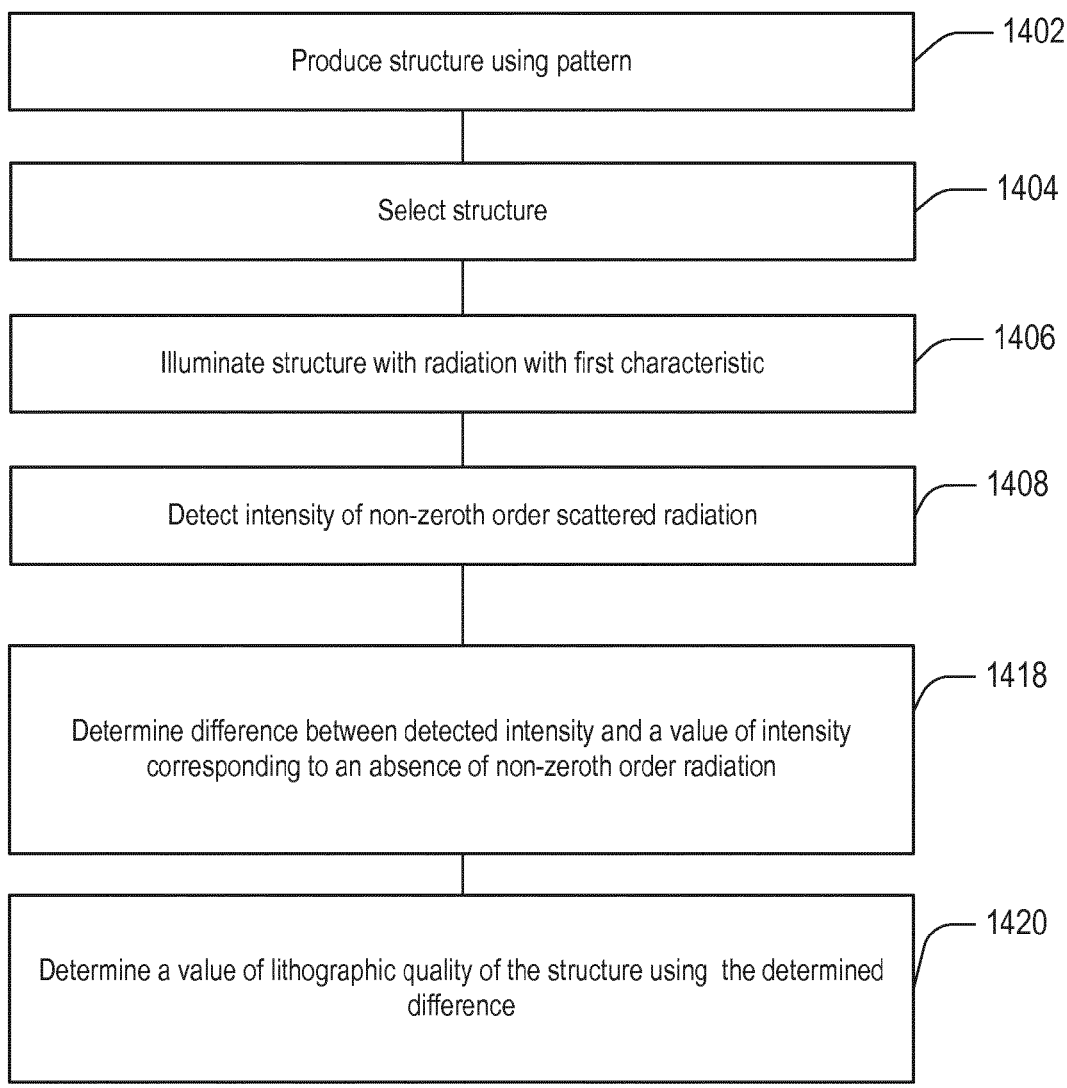
FIG. 14 is a flowchart of a method according to an example for determining lithographic quality of a structure by detecting intensity of non-zeroth order scattered radiation.

FIG. 14 is a flowchart of a method according to an example for determining lithographic quality of a structure using a periodic pattern by detecting intensity of non-zeroth order scattered radiation. It is to be appreciated the method may not occur in the order shown, or require all steps that are discussed.

FIG. 14 illustrates an example of another way to evaluate the lithographic quality of a structure. When the pitch of the printed structure is sufficiently large compared to the wavelength, high diffraction orders can be seen in the pupil. By using a pupil with a particular design, such as with an aperture with alternating light and dark quadrants of the illumination pupil, or an annular illumination pupil, the high order can be distinguished from the zeroth order. In that case, just one angularly resolved pupil can be used to detect the presence of the grating.

In step 1402: producing a structure using a lithographic process on a substrate and using a periodic pattern, such as a grating.

In step 1404: selecting the structure for illumination, such as by moving a stage supporting the substrate.

In step 1406: illuminating the structure with radiation with a first characteristic, such as TE polarization.

In step 1408: detecting intensity of non-zeroth order radiation (for example 1st, 2nd, 3rd order and so on) scattered from the structure, arising from illumination with the first characteristic, for example to measure a first angularly resolved spectrum. This may be done by spatially separating any non-zeroth order radiation scattered by the first structure to measure the intensity of the non-zeroth order radiation.

In step 1418: performing a comparison to determine a difference between the measured intensity of non-zeroth order radiation scattered by the first structure and a value of intensity corresponding to an absence of non-zeroth order radiation. The latter value may be an arbitrarily defined threshold or one obtained by calibration using a reference structure.

In step 1420: determining a value of lithographic quality of the structure using the determined difference.

The value of lithographic quality may be represented as a score, for example a grating quality score.

Examples have the following advantages: It is not required to have any previous knowledge of the stack material properties, unlike conventional scatterometry-based CD reconstruction techniques. This makes it applicable as a universal method for every new lithography process. It provides a faster way to evaluate printability in comparison with CDSEM, as a FEM wafer can be evaluated at an average of 0.5 seconds per target, whereas a CDSEM requires a time around 4 seconds per target. It provides a more reliable result in evaluating marginal printability, as it considers a number of lines within the 25 micron diameter spot of typical angularly resolved scatterometers, instead of a single line as CDSEM.

Examples provide an additional functionality of scatterometry. Examples can determine BE/BF without any previous knowledge about the gratings, with ease. Examples also improve the efficiency of setting up a new process (or characterizing an existing one) as wafers can be quickly measured in a scatterometry tool after the lithography is done, instead of requiring a long CDSEM measurement procedure.

Examples can add significant value to semiconductor manufacturers through improved usability in the lithography performance control setup and capital expenditure reduction.

Examples can be used on a stand-alone metrology tool, but running on an integrated tool is also convenient because the cluster throughput of a scanner with an integrated metrology tool may be used optimally.

The methods described herein can be implemented under the control of the processing unit PU of an inspection apparatus. The processing unit can be integrated in the scatterometer, as illustrated in FIGS. 3 and 4, or it may be located elsewhere, for example as a stand-alone unit, or distributed across apparatuses which may include the inspection apparatus.

Examples also include computer program products containing one or more sequences of machine-readable instructions for determining lithographic quality of a structure produced by a lithographic process using a periodic pattern, the instructions being adapted to cause one or more processors, such as processing unit PU of FIG. 3 or 4, and an inspection apparatus, such as an angularly resolved scatterometer of FIG. 3 or 4, to perform a method according to any of the examples described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of examples in the context of optical lithography, it will be appreciated that examples may be used in other applications, for example imprint lithography or Directed Self-Assembly lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured. In an example of the known Directed Self-Assembly lithography technique, a block copolymer is coated on a substrate that has been previously patterned with a grating of a certain pitch, then the block copolymer self assembles to form a grating of a smaller pitch, while conforming to the previously patterned larger pitch grating.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific examples have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the examples as described without departing from the scope of the clauses set out below.

It is to be appreciated that the Detailed Description section, and not the Summary and Abstract sections, is intended to be used to interpret the clauses. The Summary and Abstract sections may set forth one or more but not all exemplary embodiments of the present invention as contemplated by the inventor(s), and thus, are not intended to limit the present invention and the appended clauses in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following clauses and their equivalents.

The invention claimed is:

1. A method comprising:
illuminating a structure with a beam;
measuring intensity of non-zeroth order radiation based on the beam being scattered by the structure;
comparing the measured intensity of non-zeroth order radiation and a value of intensity corresponding to an absence of non-zeroth order radiation; and
determining a parameter of the structure based on the comparison.

2. The method of claim 1, wherein the beam is polarized.

3. An apparatus comprising:
an illumination system configured to illuminate a structure with a beam;
a detection system configured to measure intensity of the non-zeroth order radiation based on the beam being scattered by the structure; and
a processor configured to:
compare the measured intensity of non-zeroth order radiation and a value of intensity corresponding to an absence of non-zeroth order radiation, and:
determine a parameter of the structure based on the comparison.

4. The apparatus of claim 3, wherein:
the processor is further configured to perform the comparison by determining a difference between the measured intensity of non-zeroth order radiation and the value of intensity corresponding to an absence of non-zeroth order radiation.

5. The apparatus of claim 3, wherein:
the illumination system is further configured to illuminate a plurality of structures;
the detection system is further configured to measure intensities based on the beams being scattered by the plurality of structures; and
the processor is further configured to determine a process window edge of a lithographic process used to produce the plurality of the structures based on the parameters.

6. The apparatus of claim 3, wherein:
the illumination system is further configured to illuminate a plurality of structures;
the detection system is further configured to measure intensities based on the beams being scattered by the plurality of structures; and
the processor is further configured to determine an optimum process condition of a lithographic process used to produce the plurality of the structures based on the parameters.

* * * * *